United States Patent
Livingston

(10) Patent No.: US 6,282,739 B1
(45) Date of Patent: Sep. 4, 2001

(54) ADJUSTABLE HEAD REST

(75) Inventor: Sherman L. Livingston, Mesquite, TX (US)

(73) Assignee: Now Machining & Manufacturing, Dallas, TX (US)

( * ) Notice: Subject to any disclaimer, the term of this patent is extended or adjusted under 35 U.S.C. 154(b) by 0 days.

(21) Appl. No.: 09/619,011

(22) Filed: Jul. 19, 2000

(51) Int. Cl.[7] .................................. A61F 5/00; A47G 9/00
(52) U.S. Cl. ........................................ 5/640; 5/643
(58) Field of Search ................................ 5/640, 643, 636, 5/637, 638, 622; 128/857; 606/130

(56) References Cited

U.S. PATENT DOCUMENTS

| | | | |
|---|---|---|---|
| 2,239,003 | * | 4/1941 | Jones ........................................ 5/640 |
| 5,337,429 | * | 8/1994 | Tucker ...................................... 5/643 |
| 5,531,229 | * | 7/1996 | Dean et al. ............................ 606/130 |

* cited by examiner

Primary Examiner—Alexander Grosz
(74) Attorney, Agent, or Firm—Haynes and Boone, LLP

(57) ABSTRACT

An adjustable head rest for supporting the head of a patient during radiation therapy is shown. The head rest can include a table plate, an adjustable lead screw rotatably coupled to the table plate, a base plate threadably coupled to the lead screw and a uniframe including a molded member removably coupled to the base plate for supporting the head of the patient.

8 Claims, 2 Drawing Sheets

ADJUSTABLE HEAD REST

TECHNICAL FIELD

This invention relates generally to head rests, and in particular to adjustable head rests.

BACKGROUND OF THE INVENTION

Modern medicine commonly utilizes radiation therapy to treat brain tumors. In order to effectively provide such treatment, it is desirable to direct the radiation in a precise manner thereby maximizing its impact upon the tumor and minimizing unpleasant side effects to the patient. Conventional devices for supporting the head of a patient during such radiation therapy are imprecise and difficult to use.

The present invention is directed to overcoming one or more of the limitations of existing devices for supporting the head of a patient during radiation therapy.

SUMMARY OF THE INVENTION

According to one embodiment of the invention, an adjustable head rest for supporting a head of a patient during radiation therapy is provided that includes a table plate, an adjustable lead screw rotatably coupled to the table plate, a base plate threadably coupled to the lead screw, and a uniframe including a molded member removably coupled to the base plate for supporting the head of the patient.

According to another embodiment of the invention, a method of providing radiation therapy to a rear portion of a head of a patient is provided that includes supporting the front portion of the head of the patient within a molded member that matches the contours of the front portion of the head of the patient, adjusting the vertical elevation of the molded member, and deliverying a prescribed amount of radiation to the rear portion of the head of the patient.

The present embodiments of the invention provide a number of advantages. For example, the adjustable head rest provides a precise and easy to use device for supporting and controllably adjusting the vertical elevation of the head of a patient during radiation therapy. In this manner, the application of radiation to tumorous tissues within the head of the patient is provided in a precise manner thereby maximizing the effectiveness of the therapy and minimizing unpleasant side effects to the patient.

DETAILED DESCRIPTION OF THE PREFERRED EMBODIMENT

Figure 1:
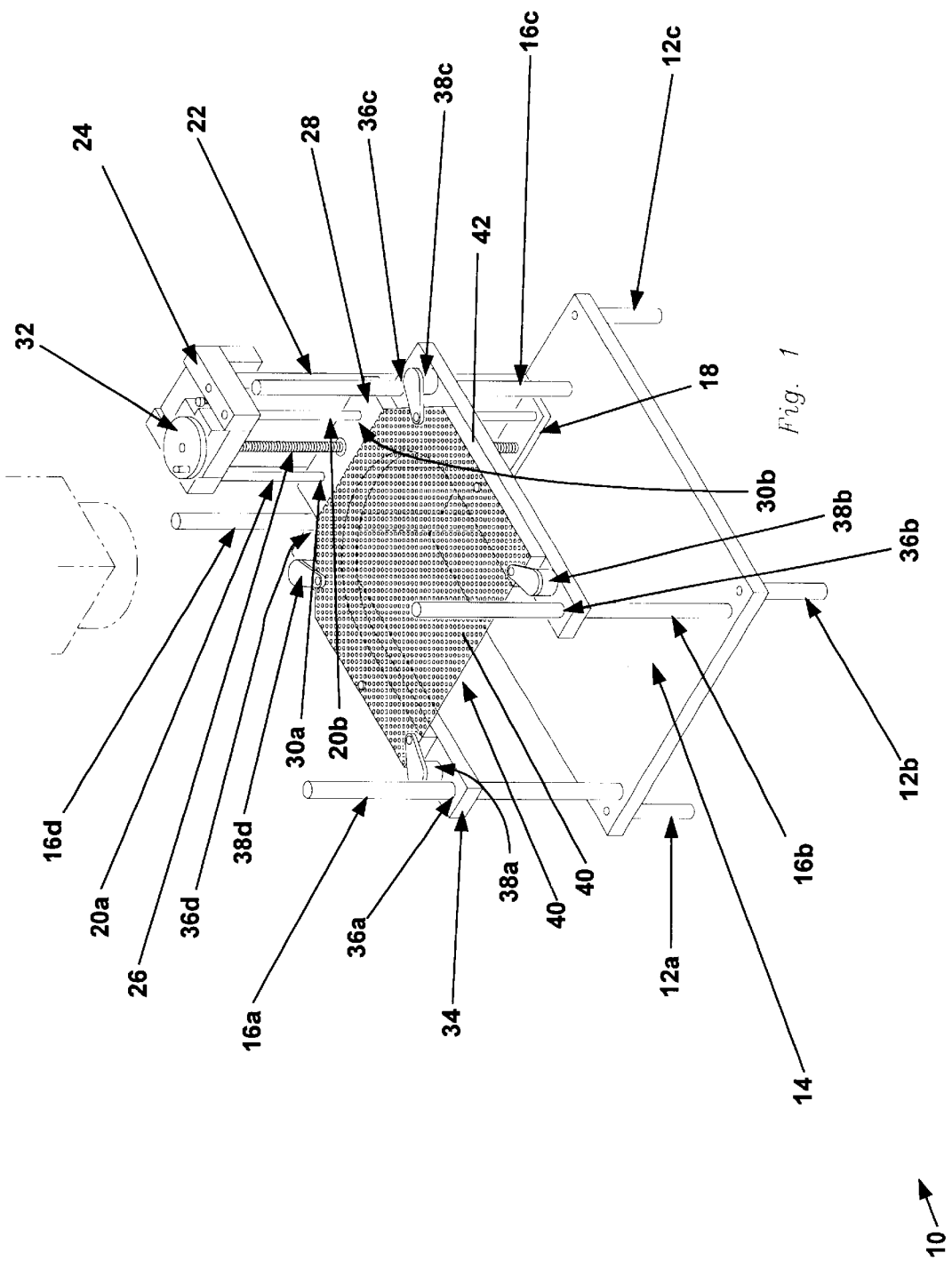
FIG. 1 is an illustration of an embodiment of an adjustable head rest for supporting the head of a patient during radiation therapy.

Referring to FIG. 1, the reference numeral 10 refers, in general, to an adjustable head rest for supporting the head of a patient during radiation therapy. The head rest 10 includes a plurality of vertically aligned post legs 12a, 12b, and 12c for supporting a horizontally aligned table plate 14 formed of aluminum (i.e. 6061 aluminum). A plurality of vertical support posts 16a, 16b, 16c, and 16d, are supported by and extend in a vertical direction from the table plate 14.

A lower support plate 18 is supported by the table plate 14. A pair of vertical support posts 20a and 20b and a vertical support member 22 are supported by and extend from the lower support plate 18. An upper support 24 is supported by the upper ends of the vertical supports 20a and 20b. An actuating lead screw 26 is rotatably supported by and extends between the lower support plate 18 and the upper support 22. A mounting bracket 28 that includes a pair of openings 30a and 30b for receiving the vertical supports, 20a and 20b, respectively is threadedly coupled to the actuating lead screw 26. An adjustment knob 32 is connected to the upper end of the actuating lead screw 26 for permitting a user to rotate the adjusting lead screw.

A U-shaped base plate 34 made of acrylic including a plurality of openings 36a, 36b, 36c, and 36d for receiving the vertical support posts 16a, 16b, 16c, and 16d, respectively, is connected to and supported by the mounting bracket 28. Swivel clamps 38a, 38b, 38c, and 38d are pivotably connected to the base plate 34 for removably attaching a uniframe 40 that includes a U-shaped support member 42 and a porous moldable thermoplastic member 44 to the base plate 34.

During operation, the uniframe 40 may be removably connected to the base plate 34 by pivotally adjusting the swivel clamps 38a, 38b, 38c, and 38d. The vertical elevation of the uniframe 40 may then be adjusted by rotating the actuating lead screw 26 using the adjustment knob 32. In particular, the rotation of the actuating lead screw 26 vertically displaces the mounting bracket 28 and base plate 34. During the vertical displacement of the mounting bracket 28, the vertical supports 20a and 20b provide lateral support to the mounting bracket, and during the vertical displacement of the base plate 34, the vertical support posts 16a, 16b, 16c, and 16d provide lateral support to the base plate. In this manner, the vertical elevation of the uniframe 36 may be adjusted.

Figure 2:
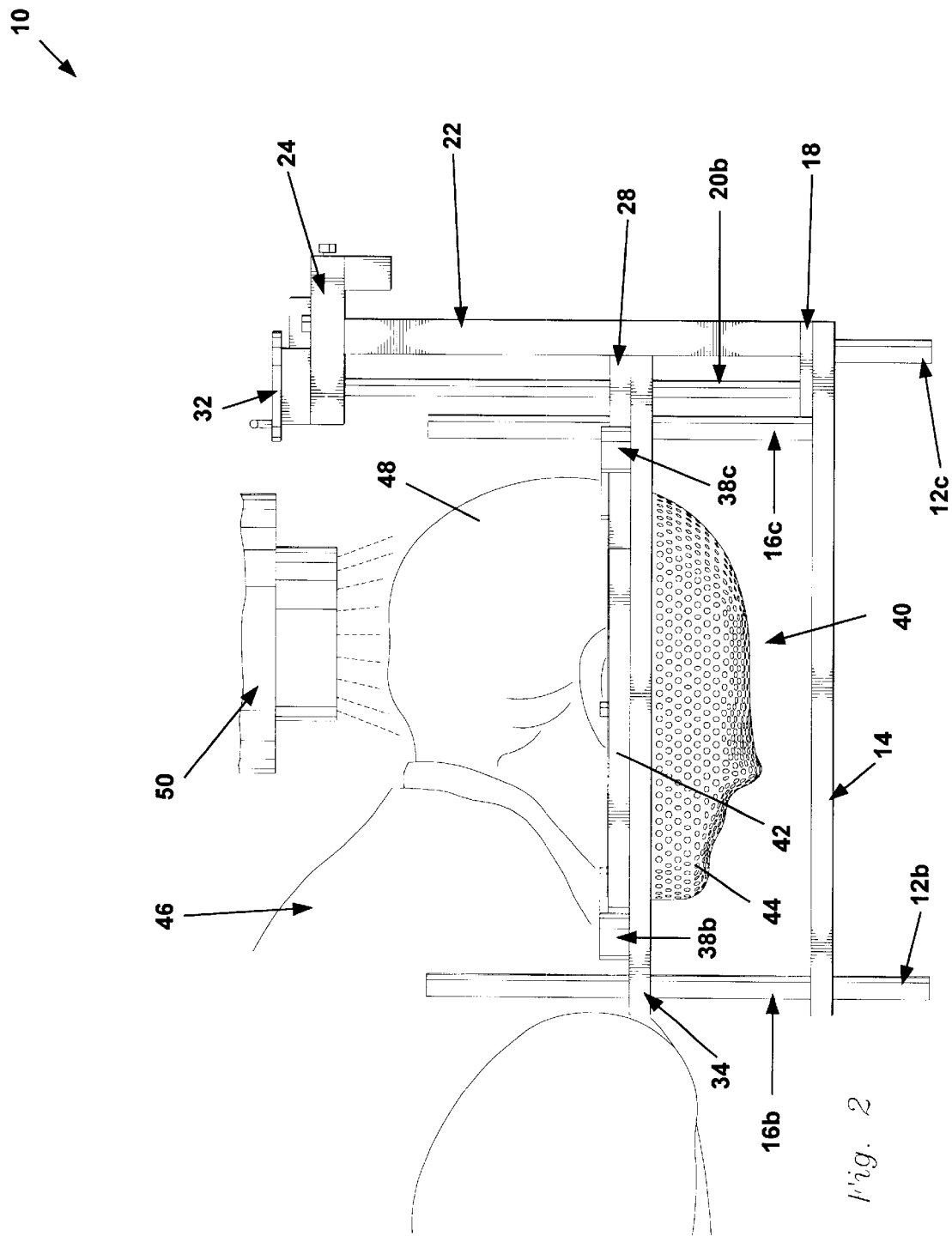
FIG. 2 is an illustration of the use of the adjustable head rest of FIG. 1 to support the head of a patient during radiation therapy.

Referring to FIG. 2, in order to provide radiation therapy to a patient 46 having a brain tumor, the moldable member 44 of the uniframe 40 is molded to match the contour of the front portion of the head 48 of the patient 46 by heating the moldable member 44 and then placing the moldable member onto the surface of the front portion of the head 48 of the patient 46 and then permitting the moldable member 44 to cool and harden. The adjustable head rest 10 is then positioned below and proximate to a conventional source of radiation 50. The uniframe 40 is then positioned onto the base plate 34 by pivotally adjusting the swivel clamps 38a, 38b, 38c, and 38d. The patient 46 is then positioned face down with the front portion of the head 48 of the patient 46 positioned within and supported by the molded member 44 of the uniframe 40 within the adjustable head rest 10. The vertical elevation of the head 48 of the patient 46 may then be adjusted by rotating the actuating lead screw 26 using the adjustment knob 32. In particular, the rotation of the actuating lead screw 26 vertically displaces the mounting bracket 28 and base plate 34. In this manner, the vertical elevation of the head 48 of the patient 46 may be adjusted thereby providing precise control of the application of the source of radiation 50. Furthermore, because the molded member 44 of the uniframe 40 matches the outer contour of the front portion of the head 48 of the patient 46, the source of radiation 50 can be precisely applied to the specific areas of head 48 of the patient 46 that include tumorous cells.

The present embodiment of the adjustable head rest provides a number of advantages. For example, the adjustable head rest provides a precise and easy to use device for supporting and controllably adjusting the vertical elevation of the head of a patient during radiation therapy. In this manner, the application of radiation to tumorous tissues within the head of the patient is provided in a precise manner thereby maximizing the effectiveness of the therapy and minimizing unpleasant side effects to the patient.

It is understood that variations may be made in the foregoing without departing from the scope of the invention. For example, the mounting bracket 28 and the base plate 34 may be unitary. In addition, other types of releasable mounting devices may be substituted for the mounting brackets 38. Furthermore, the lengths of the posts 12 may be adjustable thereby permitting the angle of inclination of the head 48 of the patient 46 to be controllably adjusted. In addition, a counter, or other visual indicator, may be added to the upper support 24 in order to provide a visual indication of the rotational position of the adjustable lead screw 26. Finally, an additional porous moldable thermoplastic member may be molded to the contours of the rear portion of the head 48 of the patient 46 and connected to the U-shaped support member 42 to thereby sandwich the head 48 of the patient 46 and provide additional support, and provide a surface on which to indicate the treatment location.

Although illustrative embodiments of the invention have been shown and described, a wide range of modification, changes, and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. An adjustable head rest for supporting a head of a patient during radiation therapy, comprising:

a table plate;

an adjustable lead screw rotatably coupled to the table plate;

a base plate threadably coupled to the lead screw; and a uniframe including a molded member removably coupled to the base plate for supporting the head of the patient.

2. The head rest of claim 1, further including:

a plurality of post legs for supporting the table plate.

3. The head rest of claim 2, wherein the lengths of the post legs are adjustable.

4. The head rest of claim 1, further including:

a plurality of vertical support members extending from the table plate for supporting the base plate.

5. The head rest of claim 1, further including:

a mounting bracket threadably coupled to the adjustable lead screw and coupled to the base plate.

6. The head rest of claim 1, further including:

a plurality of vertical support members extending from the table plate for supporting a mounting bracket.

7. The head rest of claim 6, further including:

an upper support member coupled to the vertical support members and rotatably coupled to the adjustable lead screw.

8. The head rest of claim 7, further including:

an adjustable vertical elevation of the molded member for supporting the head and wherein the head rest is used during radiation therapy.

* * * * *